United States Patent
Koehler

(10) Patent No.: US 8,660,235 B2
(45) Date of Patent: Feb. 25, 2014

(54) COMPUTED TOMOGRAPHY APPARATUS

(75) Inventor: Thomas Koehler, Norderstedt (DE)

(73) Assignee: Koninklijke Philips N.V., Eindhoven (NL)

( * ) Notice: Subject to any disclaimer, the term of this patent is extended or adjusted under 35 U.S.C. 154(b) by 50 days.

(21) Appl. No.: 13/503,870

(22) PCT Filed: Oct. 26, 2010

(86) PCT No.: PCT/IB2010/054840
§ 371 (c)(1),
(2), (4) Date: Apr. 25, 2012

(87) PCT Pub. No.: WO2011/055267
PCT Pub. Date: May 12, 2011

(65) Prior Publication Data
US 2012/0294414 A1    Nov. 22, 2012

(30) Foreign Application Priority Data
Nov. 3, 2009  (EP) .................................. 09174838

(51) Int. Cl.
*A61B 6/00* (2006.01)
(52) U.S. Cl.
USPC ............................................. 378/4; 378/901
(58) Field of Classification Search
USPC .......... 378/4, 16, 19, 145, 147, 156, 157, 901
See application file for complete search history.

(56) References Cited

U.S. PATENT DOCUMENTS

| | | | |
|---|---|---|---|
| 6,272,200 | B1 | 8/2001 | Pan et al. |
| 6,775,346 | B2 | 8/2004 | Huescher et al. |
| 6,868,138 | B2 | 3/2005 | Clinthorne et al. |
| 7,180,975 | B2 | 2/2007 | Huescher et al. |
| 7,254,216 | B2 | 8/2007 | Thandiackal et al. |
| 2004/0076265 | A1 | 4/2004 | Huescher et al. |
| 2008/0292171 | A1 | 11/2008 | Bruder et al. |

FOREIGN PATENT DOCUMENTS

| | | |
|---|---|---|
| DE | 10237546 A1 | 3/2004 |
| WO | 2004044848 A1 | 5/2004 |
| WO | 2004066215 A1 | 8/2004 |
| WO | 2008075037 A1 | 6/2008 |

OTHER PUBLICATIONS

Grass, M., et al.; Angular weighted hybrid cone-beam CT reconstruction for circular trajectories; 2001; Phys. Med. Biol.; 46:1595-1610.
Heuscher, D., et al.; Redundant data and exact helical cone-beam reconstruction; 2004; Phys. Med. Biol.; 49:2219-2238.

(Continued)

*Primary Examiner* — Jurie Yun

(57) ABSTRACT

The invention relates to a computed tomography apparatus comprising a radiation source (2) and a detector (6) for generating detection values depending on a conical radiation beam (4). A weight providing unit (12) provides, for combinations of voxels of an image and detection values, weights for weighting the detection values, and a beam shaper shapes the conical radiation beam (4) such that for at least a part of the detection values the inverse of the variance of a respective detection value is positively correlated with an average of the weights corresponding to the combinations of the voxels, which correspond to the respective detection value, and the respective detection value. This shaping of the conical radiation beam improves the signal-to-noise ratio of the weighted detection values.

14 Claims, 10 Drawing Sheets

(56) References Cited

OTHER PUBLICATIONS

Kachelriess, M., et al.; Extended parallel backprojection for standard three-dimensional and phase-correlated four-dimensional axial and spiral cone-beam CT with arbitrary pitch, arbitrary cone-angle, and 100% dose usage; 2004; Med. Phys.; 31(6)1623-1641.

Kachelriess, M., et al.; Advanced single-slice rebinning in cone-beam spiral CT; 2000; Med. Phys.; 27(4)754-772.

Matej, S., et al.; Fourier-Based Reconstruction for Fully 3-D PET: Optimization of Interpolation Parameters; 2005; 8th International Mtg. on Fully-Three Dimensional Image Reconstruction in Radiology and Nuclear Medicine; pp. 12-16.

Miracle, A. C., et al.; Conebeam CT of the Head and Neck, Part 1: Physical Principles; 2009; AJNR; pp. 1088-1095.

Riviere, P., et al.; Transmission Image Reconstruction and Redundant Information in SPECT with Asymmetric Fanbeam Collimation; 2001; IEEE; pp. 15-194-15-198.

Rohe, R. C., et al.; The Spatially-Variant Backprojection Point Kernel Function of an Energy-Subtraction Compton Scatter Camera for Medical Imaging; 1997; IEEE Trans. on Nuclear Science; 44(6)2477-2482.

Schoendube, H., et al.; Accurate helical cone-beam CT reconstruction with redundant data; 2009; Phys. Med. Biol.; 54:4625-4644.

Stierstorfer, K., et al.; Weighted FBP—a simple approximate 3D FBP algorithm for multislice spiral CT with good dose usage for arbitrary pitch; 2004; Phys. Med. Biol.; 49:2209-2218.

Taguchi, K., et al.; A new weighting scheme for cone-beam helical CT to reduce the image noise; 2004; Phys. Med. Biol.; 49:2351-2364.

Zeng, K., et al.; Correction of Iterative Reconstruction Artifacts in Helical Cone-Beam CT; 2009; 10th International Meeting on Fully Three-Dimensional Image Reconstruction in Radiology and Nuclear Medicine (Beijing, China); pp. 242-245.

COMPUTED TOMOGRAPHY APPARATUS

FIELD OF THE INVENTION

The invention relates to a computed tomography apparatus, a computed tomography method and a computed tomography computer program. The invention relates further to a beam shaper for being used with the computed tomography apparatus.

BACKGROUND OF THE INVENTION

U.S. Pat. No. 7,254,216 B2 discloses a filter assembly for a computed tomography apparatus. The filter assembly includes first and second endplates at opposite ends of the filter assembly. A first moveable subassembly includes at least a first x-ray filter and is configured to move along an axis perpendicular to the first endplate between the first the second endplates. A second moveable subassembly is also provided that includes at least a second x-ray filter. The second moveable subassembly is configured to move along an axis perpendicular to the second endplate between the first and second endplates. The first moveable subassembly and the second moveable subassembly are independently movable to provide at least a small bowtie x-ray filter, a large bowtie x-ray filter, a medium bowtie x-ray filter, a flat filter, and a closed position for a radiation source positioned in a fixed position relative to the filter assembly.

The bowtie filters are used to shape the intensity profile of an x-ray beam of the computed tomography apparatus. The intensity profile is shaped to compensate for the shape of a person's body, in particular, the intensity profile is shaped such that more photons are directed to a center of a person than to a periphery of a person, because radiation directed onto the center of the person is generally attenuated much more than the radiation directed onto the periphery of the person.

The computed tomography apparatus comprises an x-ray tube for emitting a conical x-ray beam which is filtered by the filter assembly. The filtered x-ray beam traverses a person from different directions and projection data are detected depending on the intensity of the filtered x-ray beam after having traversed the person. The computed tomography apparatus is adapted to reconstruct an image of the person from the detected projection data. The reconstructed images show artifacts which diminish the quality of the reconstructed images.

SUMMARY OF THE INVENTION

It is an object of the present invention to provide a computed tomography apparatus, a computed tomography method and a computed tomography computer program, which can improve the quality of the reconstructed images. It is a further object of the present invention to provide a beam shaper for being used with the computed tomography apparatus for allowing the computed tomography apparatus to improve the quality of the reconstructed images.

In a first aspect of the present invention a computed tomography apparatus is presented, which comprises:
- a radiation source for emitting a conical radiation beam for traversing an examination region of the computed tomography apparatus,
- a beam shaper for shaping the conical radiation beam,
- a detector for generating detection values depending on the conical radiation beam after having traversed the examination region,
- a weight providing unit for providing, for combinations of voxels of an image of the examination region and detection values, weights for weighting the detection values,
- a reconstruction unit for reconstructing the voxels, wherein for reconstructing a voxel the reconstruction unit is adapted to weight the detection values, which correspond to the voxel to be reconstructed, with the weights provided for the combinations of the voxel to be reconstructed and the respective corresponding detection value, and to reconstruct the voxel from the weighted detection values, wherein the beam shaper is adapted to shape the conical radiation beam such that for at least a part of the detection values the inverse of the variance of a respective detection value is positively correlated with an average of the weights corresponding to the combinations of the voxels, which correspond to the respective detection value, and the respective detection value.

Since the beam shaper is adapted to shape the conical radiation beam such that for at least a part of the detection values the inverse of the variance of a respective detection value is positively correlated with an average of the weights corresponding to the combination of the voxels, which correspond to the respective detection value, and the respective detection value, the beam shaper is adapted such that the signal-to-noise ratio of the weighted detection values is improved. Moreover, since this improvement is achieved by adapting the beam shaper accordingly, the weights provided by the weight providing unit can be provided without considering the signal-to-noise ratio. Therefore, the weights provided by the weight providing unit can be chosen for reducing, in particular, minimizing certain image artifacts without considering the signal-to-noise ratio, whereas the beam shaper is adapted to reduce image artifacts caused by a bad signal-to-noise ratio like a small signal-to-noise ratio or an inhomogeneous signal-to-noise ratio. The computed tomography apparatus comprising the beam shaper being adapted as described above allows therefore to improve the quality of images reconstructed by the computed tomography apparatus.

The radiation source is preferentially adapted to emit x-rays.

A voxel of an image is preferentially a three-dimensional image element of the image, wherein the image is comprised of a plurality of voxels.

The weight providing unit is preferentially adapted to provide a weight for a combination of a voxel of an image of the examination region and a detection value which corresponds to the voxel. A detection value corresponds to a voxel, if the ray of the conical radiation beam, which has caused the detection value, traverses the respective voxel. In other words, a combination of a voxel and a detection value defines a ray of the conical radiation beam. In an embodiment, for each combination of a voxel and a corresponding detection value a weight is provided.

The reconstruction unit is preferentially adapted to reconstruct a voxel of an image of the examination region by backprojecting the corresponding weighted detection values.

The beam shaper can be adapted to shape the conical radiation beam such that for a part of the detection values or for all detection values the inverse of the variance of a respective detection value is positively correlated with an average of the weights corresponding to the combinations of the voxels, which correspond to the respective detection value, and the respective detection value.

A positive correlation between the inverse variance of a detection value and an average of the weights corresponding to the combination of the voxels, which correspond to the respective detection value, and the respective detection value, means that, if the average of the weights is larger, the inverse of the variance is also larger, and, if the average of the weights is smaller, also the inverse of the variance is smaller.

The variance of a detection value is preferentially an estimated variance of the detection value. Thus, the beam shaper is preferentially adapted to shape the conical radiation beam such that for a part of the detection values or for all detection values the inverse of the estimated variance of a respective detection value is positively correlated with an average of the weights corresponding to the combinations of the voxels, which correspond to the respective detection value, and the respective detection value. The variance of a detection value is preferentially estimated by using the Poisson model.

It is preferred that the radiation source and the detector are adapted to detect redundant detection values, wherein the weight providing unit is adapted to provide, for combinations of voxels of an image of the examination region and redundant detection values normalized weights for weighting the redundant detection values, wherein for reconstructing a voxel the reconstruction unit is adapted to weight the redundant detection values, which correspond to the voxel to be reconstructed, with the normalized weights provided for the combinations of the voxel to be reconstructed and the respective corresponding redundant detection value, and to reconstruct the voxel from the weighted redundant detection values, wherein the beam shaper is adapted to shape the conical radiation beam such that for at least a part of the redundant detection values the inverse of the variance of a respective redundant detection value is positively correlated with an average of the weights corresponding to the combination of the voxels, which correspond to the respective redundant detection value, and the respective redundant detection value.

Redundant detection values are detection values which have been generated at different times, while the radiation, on which the respective detection value depends, has travelled through the examination region along the same way in possibly different directions.

The normalized weights are preferentially normalized such that the sum of the weights of redundant detection values, which correspond to the same voxel, is one. Preferentially, for each combination of a voxel and a corresponding redundant detection value a normalized weight is provided. Preferentially, for reconstructing a voxel the reconstruction unit is adapted to i) weight redundant detection values, which correspond to the voxel to be reconstructed, wherein the redundant detection values are multiplied with the normalized weights provided for the combination of the voxel to be reconstructed and the respective corresponding redundant detection value, and ii) reconstruct the voxel from the weighted redundant detection values. The reconstruction unit is preferentially adapted to reconstruct a voxel of an image of the examination region by backprojecting the corresponding weighted redundant detection values and preferentially also further non-redundant detection values, if present.

It is further preferred that the beam shaper is adapted to shape the conical radiation beam such that for at least a part of the detection values the intensity of the part of the conical radiation beam, on which the respective detection value depends, before traversing the examination region is positively correlated with the average of the weights corresponding to the combination of the voxels, which correspond to the respective detection value, and the respective detection value, for ensuring that for at least a part of the detection values the inverse of the variance of a respective detection value is positively correlated with an average of the weights corresponding to the combination of the voxels, which correspond to the respective detection value, and the respective detection value. It is assumed that the inverse of the variance is proportional, in particular, similar, to the intensity before traversing the examination region. This allows therefore simply designing the beam shaper depending on the intensity of the respective part of the conical radiation beam, without explicitly determining, in particular, estimating, the inverse variance of a detection value.

It is preferred that the weight providing unit is adapted to provide the weights such that cone-beam artifacts are reduced. In particular, the weight providing unit is preferentially adapted to optimize the weights such that cone-beam artifacts are reduced, wherein the weights can be optimized without considering the signal-to-noise ratio. This further improves the quality of the reconstructed images.

It is further preferred that the weight providing unit is adapted to provide the weights such that motion artifacts are reduced. In particular, the weight providing unit can be adapted to provide weights which are optimized for reducing motion artifacts which are caused by a movement of an object within the examination region, without considering the signal-to-noise ratio. This further improves the quality of images reconstructed by using the computed tomography apparatus.

In an embodiment, the weight providing unit is adapted to provide the weights such that cone-beam artifacts and motion artifacts are reduced, in particular, preferentially these weights are predetermined without considering the signal-to-noise ratio.

It is further preferred that the weight providing unit is adapted to provide a weight for a combination of a voxel and a detection value depending on the aperture of the part of the conical radiation beam, which has traversed the voxel and on which depending the detection value has been generated. It is further preferred that the weight providing unit is adapted to provide a larger weight, if the aperture is smaller, and a smaller weight, if the aperture is larger.

Since detection values, which correspond to a larger aperture, cause generally more pronounced cone-beam artifacts than detection values corresponding to a smaller aperture by weighting detection values having a smaller aperture with a larger weight than detection values having a larger aperture, the cone-beam artifacts can be reduced. The aperture weighting therefore further improves the quality of the reconstructed images.

A projection is preferably defined as a group of detection values, which have been acquired at the same time while the radiation source was arranged at the same location.

It is further preferred that the weight providing unit is adapted to provide the weights such that the weights of the detection values continuously and monotonically approach zero with increasing aperture. This allows avoiding non-continuity of the weights as a function of time, thereby suppressing motion artifacts. For example, in particular, if the detection values are redundant detection values and if the corresponding weights are normalized weights, this aperture weighting function ensures that the contribution of a projection to the reconstruction results continuously fades out as the projected voxel position approaches the border of the detector panel. This continuous out-fading corresponds to a continuous in-fading of redundant detection values since the sum of weights for all redundant detection values of a voxel is enforced to be one. By this, it is ensured that the weighting of detection values is a continuous function of time as well, because the projected voxel position depends continuously on the projection angle and thus on time. By avoiding any non-continuity of the weights as a function of time, motion artifacts are suppressed.

Monotonically approaching zero means that the weights are constant or decrease with increasing aperture, but they do not increase with increasing aperture.

The computed tomography apparatus comprises preferentially a moving unit for rotating the radiation source and the examination region relative to each other around a rotational axis, wherein the detector generates the detection values during this rotational movement.

The aperture of a part of a conical radiation beam, i.e. of a ray of the conical radiation beam, is the aperture angle of the ray of the conical radiation beam. The aperture angle is defined by the angle between the ray and a plane perpendicular to the rotational axis of the computed tomography apparatus.

The moving unit is preferentially adapted to move the radiation source and the examination region relative to each other along a helical trajectory, wherein the weight providing unit is adapted to provide the weights depending on the pitch of the helical trajectory, wherein the computed tomography apparatus comprises several beam shapers for different pitches and is adapted to choose a beam shaper from the several beam shapers depending on the pitch of the helical trajectory and to use the chosen beam shaper while generating the detection values. This allows the computed tomography apparatus to acquire the detection values along different helical trajectories having different pitches, wherein for the different pitches different beam shapers can be provided for improving the signal-to-noise ratio.

The pitch is preferentially defined as the relative physical travel of the examination region and the computed tomography apparatus per rotation divided by the total collimation of the detector. The collimation of the detector is preferentially defined as the detector height (i.e., the physical dimension of the detector in the direction of the rotation axis) projected into the isocenter of the computed tomography apparatus.

It is further preferred that the computed tomography apparatus comprises a collimator for collimating the conical radiation beam, wherein the weight providing unit is adapted to provide the weights depending on a collimation of the conical radiation beam, wherein the computed tomography apparatus comprises several beam shapers for different collimations and is adapted to choose a beam shaper from the several beam shapers depending on the collimation of the conical radiation beam and to use the chosen beam shaper while generating the detection values. This allows the computed tomography apparatus to acquire the detection values with different collimations, wherein for the different collimations different beam shapers can be provided for improving the signal-to-noise ratio.

It is further preferred that the beam shaper is adapted such that the at least part of the detection values for which the inverse of the variance of a respective detection value is positively correlated with an average of the weights corresponding to the combination of the voxels, which correspond to the respective detection value, and the respective detection value, corresponds to a part of the conical radiation beam around the center of the conical radiation beam with respect to the direction of the rotational axis. This ensures that within the center of the conical radiation beam, in which generally a region of interest to be reconstructed is located, the signal-to-noise ratio is improved. This leads to reconstructed images, wherein at least the part of the examination region located within a central part of the conical radiation beam is reconstructed with an improve signal-to-noise ratio. That means at least the generally most important part of the examination region being the region of interest is reconstructed with an improved signal-to-noise ratio.

The beam shaper can be a bowtie filter. The beam shaper can therefore fulfill two functions, improving the signal-to-noise ratio and adjusting the beam shape to the general shape of a person.

It is preferred that the computed tomography apparatus further comprises a second kind of beam shaper being a bowtie filter. The computed tomography apparatus comprises therefore, in an embodiment, at least one beam shaper of a first kind, wherein the beam shaper of the first kind is adapted to shape the conical radiation beam such that for at least a part of the detection values the inverse of the variance of a respective detection value is positively correlated with an average of the weights corresponding to the combination of the voxels, which correspond to the respective detection value, and the respective detection value, and separately at least one beam shaper of a second kind being a bowtie filter. This allows using the same bowtie filter with one or several beam shapers of the first kind. For example, for different pitches of a helical trajectory and/or different collimations different beam shapers can be provided, wherein for the different helical trajectories with the different pitches and/or the different collimations the same bowtie filter can be used.

In a further aspect of the present invention a beam shaper for being used with a computed tomography apparatus as defined in claim 1 is presented, wherein the beam shaper is adapted to shape the conical radiation beam such that for at least a part of the detection values the inverse of the variance of a respective detection value is positively correlated with an average of the weights corresponding to the combination of the voxels, which correspond to the respective detection value, and the respective detection value.

In a further aspect of the present invention a computed tomography method is presented, wherein the computed tomography method comprises following steps:
  emitting a conical radiation beam for traversing an examination region of a computed tomography apparatus by a radiation source,
  shaping the conical radiation beam by a beam shaper,
  generating detection values depending on the conical radiation beam after having traversed the examination region by a detector,
  providing, for combinations of voxels of an image of the examination region and detection values, weights for weighting the detection values by a weight providing unit,
  reconstructing the voxels by a reconstruction unit, wherein for reconstructing a voxel the detection values, which correspond to the voxel to be reconstructed, are weighted with the weights provided for the combinations of the voxel to be reconstructed and the respective corresponding redundant detection value, and the voxel is reconstructed from the weighted detection values,
wherein the conical radiation beam is shaped such that for at least a part of the detection values the inverse of the variance of a respective detection value is positively correlated with an average of the weights corresponding to the combinations of the voxels, which correspond to the respective detection value, and the respective detection value.

In a further aspect of the present invention a computed tomography computer program is presented, wherein the computed tomography computer program comprises program code means for causing a computed tomography apparatus as defined in claim 1 to carry out the steps of the computed tomography method as defined in claim 14, when the computed tomography computer program is run on a computer controlling the computed tomography apparatus.

It shall be understood that the computed tomography apparatus of claim 1, the beam shaper of claim 13, the computed tomography method of claim 14 and the computed tomography computer program of claim 15 have similar and/or identical preferred embodiments as defined in the dependent claims.

It shall be understood that a preferred embodiment of the invention can also be any combination of the dependent claims with the respective independent claim.

These and other aspects of the invention will be apparent from and elucidated with reference to the embodiments described hereinafter.

DETAILED DESCRIPTION OF EMBODIMENTS

Figure 1:
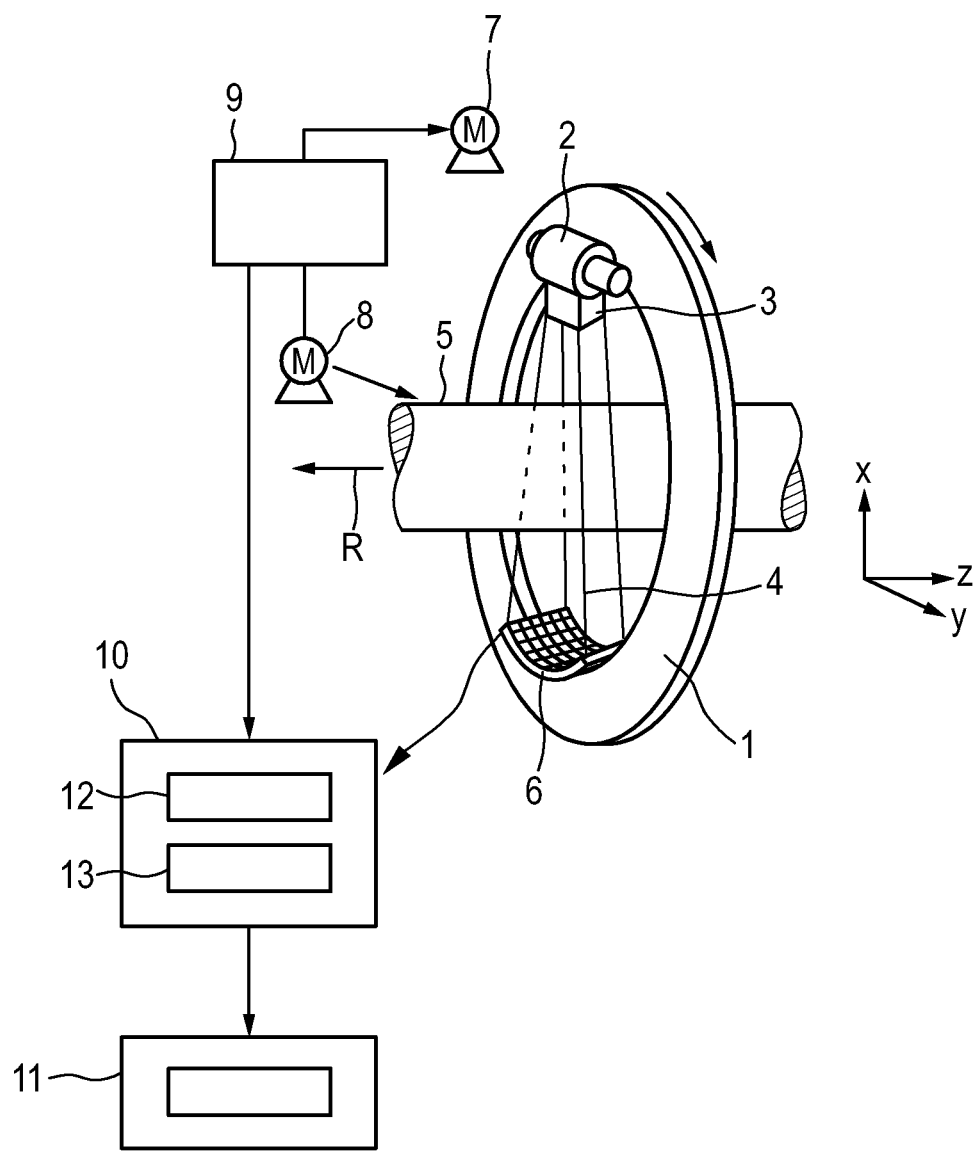
FIG. 1 shows schematically and exemplarily a computed tomography apparatus.

FIG. 1 shows schematically and exemplarily a computed tomography apparatus including a gantry 1 which is capable of rotation about a rotational axis R which extends parallel to a z direction. A radiation source 2, which is, in this embodiment, an x-ray tube, is mounted on the gantry 1. The radiation source 2 is provided with a collimation and shaping unit 3 which forms a conical radiation beam 4 from the radiation generated by the radiation source 2 and shapes the intensity profile within the conical radiation beam 4. The radiation traverses an object (not shown) such as a patient in an examination region 5 which is, in this embodiment, cylindrical. After having traversed the examination region 5 the conical radiation beam 4 is incident on a detector 6 which comprises a two-dimensional detection surface. The detector 6 is mounted on the gantry 1.

The computed tomography apparatus comprises two motors 7, 8. The gantry 1 is driven at a preferably constant but adjustable angular speed by the motor 7. The motor 8 is provided for displacing the object, for example, a patient, who is arranged on a patient table in the examination region 5, parallel to the direction of the rotational axis R or the z axis. These motors 7, 8 are controlled by a control unit 9, for instance, such that the radiation source 2 and the examination region 5 move relative to each other along a helical trajectory. However, it is also possible that the object or the examination region 5 is not moved, but that only the radiation source 2 is rotated, i.e. that the radiation source 2 moves along a circular trajectory relative to the object or the examination region 5.

The gantry 1 and the motors 7, 8 can be regarded as a moving unit for moving the radiation source 2 and the examination region 5 relative to each other along a trajectory, in particular along a circular or helical trajectory.

During a relative movement of the radiation source 2 and the examination region 5 the detector 6 generates detection values depending on the radiation incident on the detection surface of the detector 6. The radiation source 2 and the detector 6 are moved such that redundant detection values are detected, i.e. they are moved such that a first detection value is generated by the radiation of a ray of the conical radiation beam traversing the examination region 5 along a certain path and a second detection value is generated by a ray of the conical radiation beam traversing the examination region 5 along the same certain path. Detection values, which correspond to the same path through the examination region 5 and which have been acquired at different times, are regarded as being redundant detection values.

The detection values, which are, in this embodiment, projection data, are provided to an image generation device 10 for generating an image of the examination region 5, in particular, of a region of interest within the examination region 5, from the detection values, i.e. from the projection data. The region of interest is located within the examination region 5 and preferentially contains an object or a part of an object. The image generation device 10 comprises a weight providing unit 12 for providing, for combinations of voxels of an image of the examination region 5 and redundant detection values, normalized weights for weighting the redundant detection values. In this embodiment, the weight providing unit 12 is adapted to provide the normalized weights such that cone-beam artifacts and motion artifacts are reduced. This reduction of cone-beam artifacts and motion artifacts is obtained by providing a normalized weight for a combination of a voxel and a detection value depending on the aperture of the part of the conical radiation beam, in particular, of the ray of the conical radiation beam, which has traversed the voxel and on which depending the detection value has been generated. In particular, the weight providing unit 12 is adapted to provide a larger weight, if the aperture is smaller, and a smaller weight, if the aperture is larger.

The gantry 1 and the motors 7, 8 are preferentially adapted to allow the radiation source 2 and the examination region 5 to move relative to each other along helical trajectory having different pitches. For example, during a first acquisition of detection values for reconstructing a first image of the examination region 5 the radiation source 2 and the examination region 5 can be moved relative to each other along a first helical trajectory having a first pitch and during a second acquisition of detection values for reconstructing a second image of the examination region 5 the radiation source 2 and the examination region 5 can be moved relative to each other along a second helical trajectory having a second pitch being different to the first pitch. The weight providing unit 12 is preferentially adapted to provide the normalized weights depending on the pitch of the helical trajectory.

The collimation and shaping unit 3 is preferentially adapted to modify the collimation of the conical radiation beam 4. Thus, the collimation and shaping unit 3 is preferentially adapted to collimate the conical radiation beam 4 from the radiation generated by the radiation source 2 and to modify the collimation of the conical radiation beam 4. The weight providing unit 12 is preferentially adapted to provide the normalized weights depending on the actual collimation of the conical radiation beam 4.

The weight providing unit is preferentially further adapted to provide the normalized weights such that the weights of the detection values continuously and monotonically approach zero with increasing aperture.

The weight providing unit and the reconstruction unit are preferentially adapted to perform an aperture weighted wedge method.

In the aperture weighted wedge method, backprojection is described most conveniently in the gantry's coordinate system, i.e., in a system where the source detector arrangement is fixed and the voxel moves on a helical path through the system. The axis of rotation is the z-axis, the y-axis is parallel to the projection direction and the x-axis is chosen such that a right-handed coordinate system is created. Coordinates in x and y are scaled such that the distance of the x-ray source to the z-axis is equal to one. The projection of a voxel at position $(x_0, y_0, z_0)$ can then be defined by following equations:

$$u = x_0 \text{ and } v = \frac{z_0 - p \arcsin x_0}{\sqrt{1 - x_0^2} - y_0} \tag{1}$$

where p is the pitch divided by $2\pi$, u is the fan direction, which might be a rebinned fan direction, on the detector and v is the coordinate along the direction of the z-axis. The location v=0 corresponds to a voxel that is projected at an aperture angle of zero degrees. Aperture weighting is preferentially implemented by specifying a so-called aperture weighting function a(v), that has the basic features described already, namely that is has its maximum for v=0 and it decreases monotonically and continuously to zero when v approaches the border of the detector panel. Practically, a trapezoidal shape can be used. Normalized weights are calculated by "brute-force" normalization of all redundant rays. In the concept of the wedge algorithm, all rays through the voxel at projection angles which are integer multiples of it apart from the view under consideration are considered to be redundant. The normalized weight for the current projection, where the voxel is at the position $(x_0, y_0, z_0)$, is preferentially defined by following equation:

$$w_0 = \frac{a\left(\frac{z_0 - p\arcsin x_0}{\sqrt{1 - x_0^2} - y_0}\right)}{\sum_i a\left(\frac{z_i - p\arcsin x_i}{\sqrt{1 - x_i^2} - y_i}\right)} \tag{2}$$

where in the denominator the voxel positions $(x_i, y_i, z_i)$ are related to all redundant voxel positions including the current position.

The fan direction is the direction of the rays in a plane perpendicular to the rotation axis R or the z axis. The rebinning is a parallel rebinning, wherein detection values are sorted and interpolated such that a projection consists of detection values with corresponding parallel rays within a plane perpendicular to the rotational axis or the z axis.

Referring again to FIG. 1, the computed tomography apparatus further comprises a reconstruction unit 13 for reconstructing the voxels of an image of the examination region 5. The reconstruction unit is adapted to perform following steps for reconstructing a voxel: i) weighting redundant detection values which correspond to the voxel to be reconstructed, wherein the redundant detection values are multiplied with the normalized weights provided for the combinations of the voxel to be reconstructed and the respective corresponding redundant detection value, and ii) reconstructing the voxel from the weighted redundant detection values, in particular, by backprojecting the weighted redundant detection values and preferentially also non-redundant detection values, if present. The reconstruction is preferentially performed by using a backprojection algorithm.

The image reconstructed by the reconstruction unit 13 is provided to a display unit 11 for displaying the reconstructed image.

Also the image generation device 10 is preferentially controlled by the control unit 9.

In the following the collimation and shaping unit 3 will be described in more detail with reference to FIG. 2.

Figure 2:
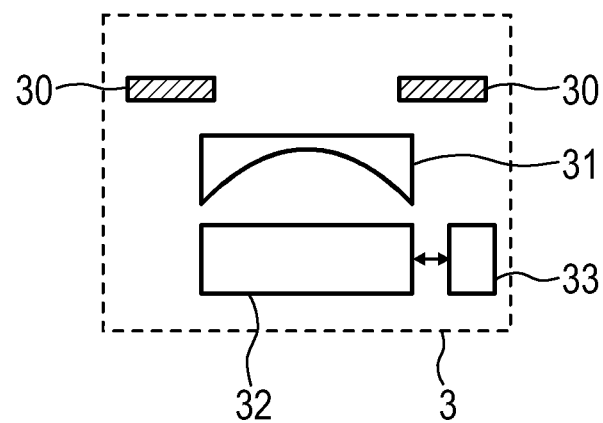
FIG. 2 shows schematically and exemplarily a collimation and shaping unit comprising a beam shaper viewed along a z-axis.
Figure 2:

FIG. 2 shows schematically and exemplarily the collimation and shaping unit 3 in the direction of the z-axis. The collimation and shaping unit 3 comprises a collimator 30 for collimating the radiation generated by the radiation source 2 such that the conical radiation beam 4 is generated.

The collimator 30 is preferentially made of a high-Z material like tungsten in order to absorb efficiently all the x-rays that are supposed to be blocked.

The collimation and shaping unit 3 further comprises a beam shaper 32 being adapted to shape the conical radiation beam 4 such that for at least a part of the detection values the inverse of the variance of a respective detection value is positively correlated with an average of the normalized weights corresponding to the combination of the voxels, which correspond to the respective detection value, and the respective detection value. In particular, the beam shaper 32 is preferentially adapted such that the at least part of the detection values for which the inverse of the variance of a respective detection value is positively correlated with an average of the normalized weights corresponding to the combination of the voxels, which correspond to the respective detection value, and the respective detection value, corresponds to a part of the conical radiation beam around the center of the conical radiation beam 4 with respect to the direction of the rotational axis. The beam shaper is adapted to substantially not impose an intensity modulation in fan direction, i.e. in a direction within a plane perpendicular to the z-axis.

Figure 3:
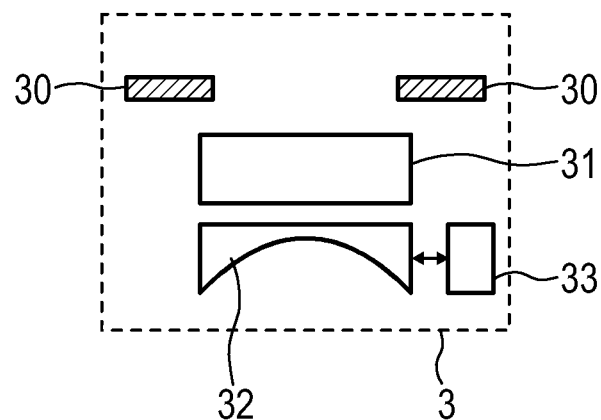
FIG. 3 shows schematically and exemplarily the collimation and shaping unit in a direction being perpendicular to the z-axis.
Figure 3:
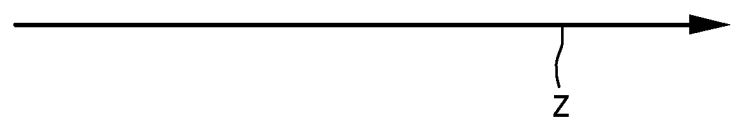

FIG. 3 shows schematically and exemplarily the collimation and shaping unit 3 in a direction being perpendicular to the z-axis. As can be seen in FIG. 3, the beam shaper 32 is adapted to impose an intensity modulation in cone direction, i.e. in a direction in a plane defined by the z-axis and the position of the radiation source.

As already mentioned above, a voxel at position $(x_0, y_0, z_0)$ gets the normalized backprojection weight $w_0$ according to equation (2). This weighting is calculated on a per-voxel basis. This means that another voxel $(x_a, y_a, z_a)$ that is projected onto the same detector position as the voxel $(x_0, y_0, z_0)$ will get a different normalized weight. Due to the projection geometry all voxels which are projected onto the same detector location are located on a straight line connecting the source position and the detector coordinate. The average normalized weight associated with a detector value corresponding to the coordinates $(u_0, v_0)$ can be calculated by averaging over all voxels on this line, where the line should be further limited to the part which intersects the examination region 5, i.e. it should be limited to all voxels which never leave the cone-beam in fan-direction.

Figure 4:
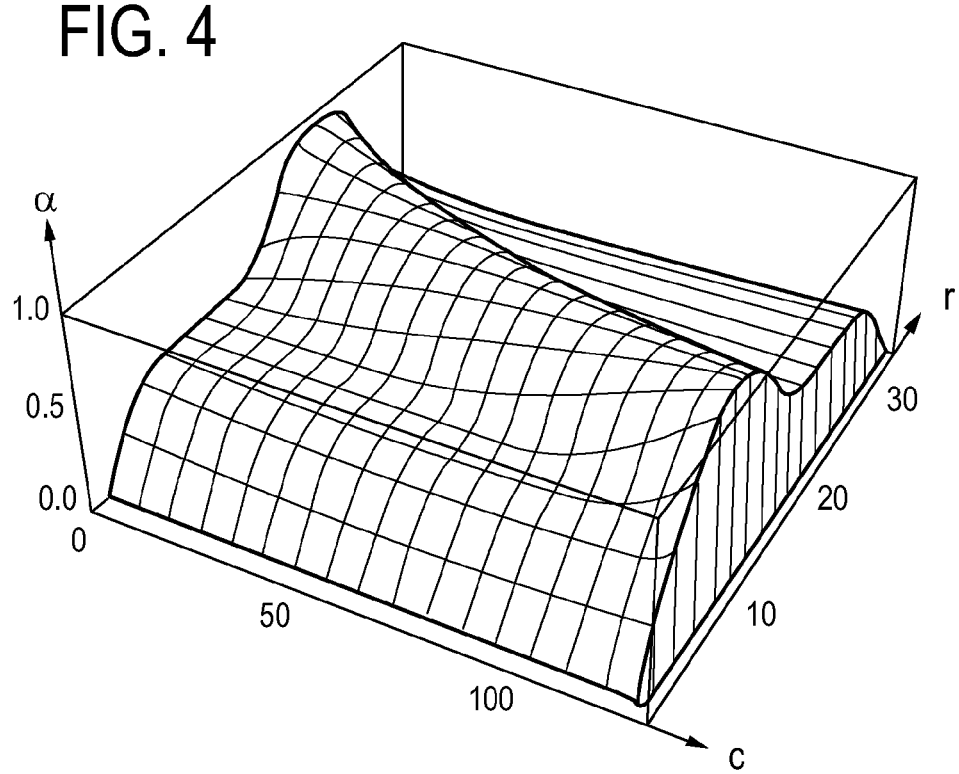
FIG. 4 shows schematically and exemplarily averaged normalized weights.

Averages of the normalized weights, which have been determined for different detection values, are schematically and exemplarily shown in FIG. 4. In FIG. 4, different detection values are indicated by their position on the detection surface. The position on the detection surface is indicated by the detector column c which corresponds to the above mentioned u coordinate and the detector row r which corresponds to the above mentioned v coordinate. The axis indicated in FIG. 3 by r is parallel to the rotational axis R. In a natural scaling of the coordinate system, u and v are given in units of the detector pixel width and height, i.e., a detector pixel (projected into the isocenter) has width and height 1. This natural scaling facilitates a convenient addressing of detector rows and columns by the simple relation r=v+(number rows−1)/2 and c=u+(number columns−1)/2. The averaged normalized weights a approach zero at the edges of the detection surface, which are perpendicular to the axis indicated by r or the rotational axis R. The detection values at these edges correspond to outermost parts of the conical radiation beam 4 in the direction of their rotational axis R, i.e. the detection values and these edges correspond to parts of the conical radiation beam having the largest absolute aperture. The averaged normalized weights are independent of the rotational position of the radiation source 2 and depend preferentially on the collimation of the conical radiation beam 4 and/or the pitch of a helical trajectory.

As already mentioned above, the beam shaper 32 is adapted to shape the conical radiation beam 4 such that for at least a part of the detection values the inverse of the variance of a respective detection value is positively correlated with the average of the normalized weights corresponding to the combination of the voxels, which correspond to the respective detection value, and the respective detection value. In particular, a detection value is caused by a ray of the conical radiation beam, which traverses the examination region 5 and which is incident on a respective detector element of the detector 6. The beam shaper is adapted to shape the conical radiation beam such that the inverse of the variance of the respective detection value is positively correlated with an average of the normalized weights corresponding to the combinations of the voxels along the ray and the respective detection value.

The variance of detection values is estimated preferentially using the Poisson model. Let $I_0$ denote the mean number of photons emitted towards a detector pixel. Due to the attenuation of the beam by the patient, only I photons reach the detector pixel on average. Still the number of photons follows the Poisson statistics. Thus, the variance of the detected signal is I. For reconstruction, a so-called line integral through the total attenuation coefficient is estimated by using the formula $$m = -\log(I/I_0). \tag{3}$$

For the following discussion, the variance of the derived quantity m is estimated by means of Gaussian error propagation $$\delta m = \frac{\partial}{\partial I} m(I) \delta I = \frac{1}{I} \delta I \tag{4}$$

resulting in $$\mathrm{var}(m) = (\delta m)^2 = \left(\frac{1}{I}\right)^2 (\delta I)^2 = \left(\frac{1}{I}\right)^2 \mathrm{var}(I) = \frac{1}{I} = \frac{1}{\mathrm{var}(I)}. \tag{5}$$

The mean number of photons emitted towards a detector pixel is the intensity of the respective part of the conical radiation beam 4, on which the respective detection value of the detection pixel depends, before traversing the examination region 5. This intensity or mean number of photons can be determined from air scans. An air scan is an acquisition of detection values without an object present in the examination region 5.

In order to achieve the best possible signal-to-noise ratio during averaging of redundant detection values following relation should be fulfilled, wherein the bar over the weight $w_0$ indicates the average weight:

$$\overline{w}_0 \propto \frac{1}{\mathrm{var}(m)} = \mathrm{var}(I). \tag{6}$$

The general assumption for redundant detection values is that the total attenuation along the corresponding ray paths was the same, meaning that the fraction f of photons that reaches the detector is the same for all redundant rays. In other words, we can write $$\overline{w}_0 \partial \mathrm{var}(I) = I = fI_0. \tag{7}$$

Since the fraction f is assumed to be the same for all redundant rays, it will cancel out during normalization of the weights, resulting in $$\overline{w}_0 \partial I_0. \tag{8}$$

The beam shaper is therefore preferentially adapted to provide the initial, non-attenuated intensity $I_0$ is such that the relation defined in equation (8) is fulfilled. The beam shaper is preferentially made of a homogenous material with a constant attenuation coefficient. The required thickness distribution of the beam shaper for shaping the intensity profile of the conical radiation beam such that equation (8) is fulfilled can therefore be calculated by using Beers law.

Figure 5:
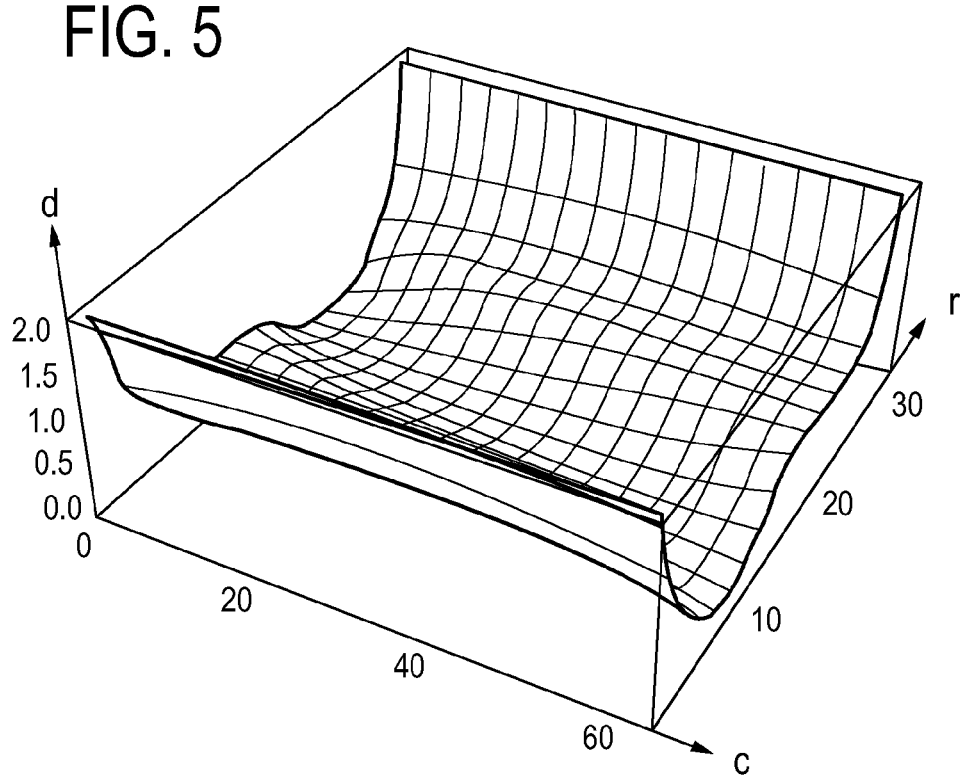
FIG. 5 illustrates schematically and exemplarily a thickness distribution of a beam shaper.

FIG. 5 illustrates schematically and exemplarily a thickness d of a beam shaper which is adapted to shape the conical radiation beam such that for at least a part of the detection values the inverse of the variance of a respective detection value is positively correlated with an average of the normalized weights corresponding to the combination of the voxels, which correspond to the respective detection value, and the respective detection value.

The computed tomography apparatus comprises preferentially several beam shapers for different pitches and/or for different collimations, wherein the computed tomography apparatus is adapted to chose a beam shaper from the several beam shapers depending on the pitch of the helical trajectory and/or the collimation of the conical radiation beam 4, respectively, and to use the chosen beam shaper while generating the detection values. For choosing an appropriate beam shaper, the collimation and shaping unit 3 comprises a beam shaper exchange unit 33 for exchanging a beam shaper actually located within the path of the conical radiation beam by another beam shaper. The beam shaper exchange unit 33 can be a sliding unit on which several beam shapers are mounted side by side, wherein the desired beam shaper can be located within the beam by sliding the beam shaper to the desired position. The sliding unit is preferentially slidable along the z-axis.

Figure 6:
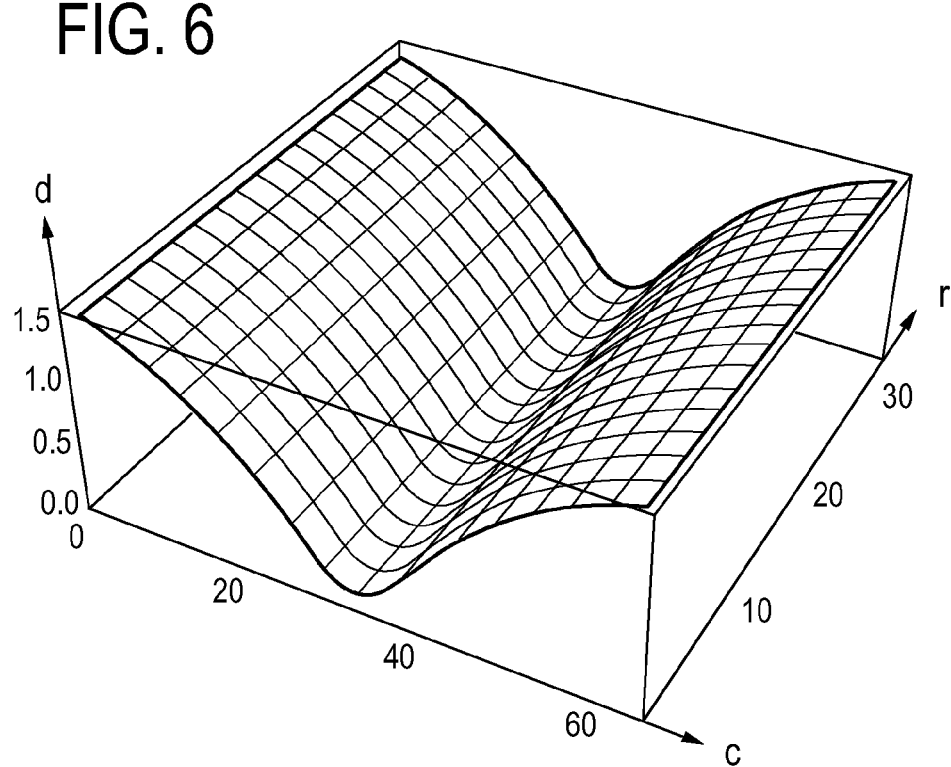
FIG. 6 illustrates schematically and exemplarily a thickness distribution of a bowtie filter.

Referring again to FIGS. 2 and 3, the computed tomography apparatus further comprises a bowtie filter 31 which can, in comparison to the beam shaper 32, be regarded as a second kind of beam shaper. The bowtie filter 31 is adapted to impose an intensity modulation in fan direction and to not impose an intensity modulation in cone direction. FIG. 6 illustrates schematically and exemplarily the thickness d of a bowtie filter. As can be seen in FIG. 6, the bowtie filter is preferentially adapted such that radiation corresponding to small fan angles is less attenuated than radiation corresponding to larger fan angles, i.e. radiation causing detection values in the middle of the detector surface with respect to the c axis are attenuated less than radiation which causes detection values at the edges of the detector surface with respect to the c axis.

The combination of the bowtie filter and the beam shaper can be replaced by a single beam shaper being a bowtie filter, i.e. a second kind of beam shaper, and a beam shaper being adapted to shape the conical radiation beam such that for at least a part of the detection values the inverse of the variance of a respective detection value is positively correlated with an average of the weights corresponding to the combinations of the voxels, which correspond to the respective detection value, and the respective detection value, which can be regarded as a first kind of beam shaper. This beam shaper fulfills therefore two functions and can be regarded as a bowtie filter which is adapted as described above to shape the conical radiation beam such that for at least a part of the detection values the inverse of the variance of a respective detection value is positively correlated with an average of the weights corresponding to the combination of the voxels, which correspond to the respective detection value, and the respective detection value. A thickness distribution of such a beam shaper is schematically and exemplarily illustrated in FIG. 7. A beam shaper exchange unit can be provided for choosing this beam shaper depending on the collimation of the conical radiation beam and/or the pitch of a helical trajectory.

Figure 7:
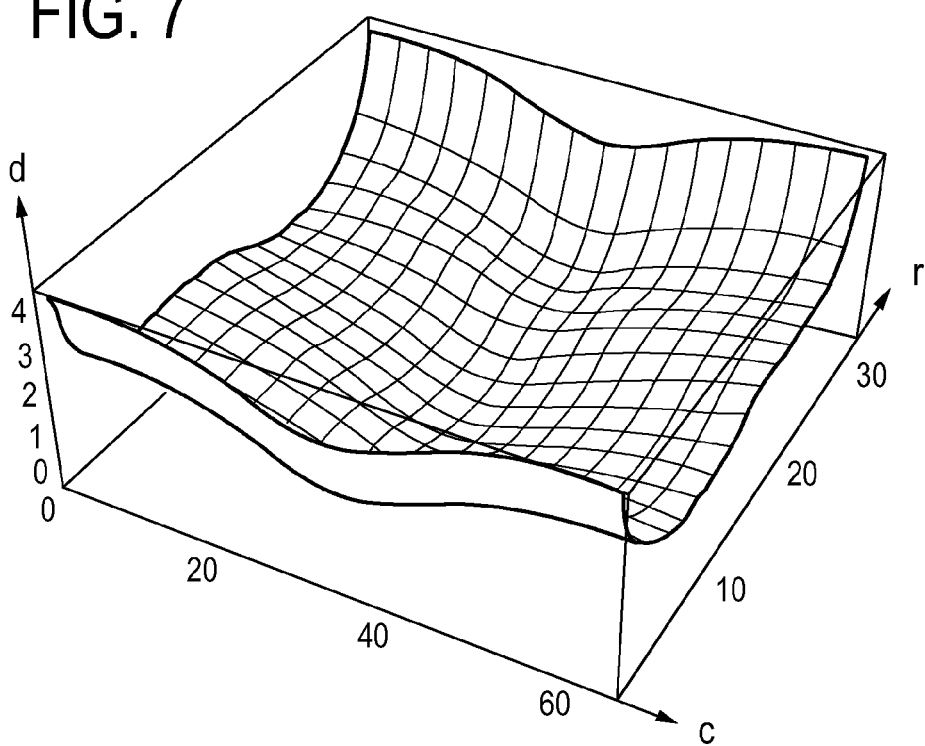
FIG. 7 illustrates schematically and exemplarily a thickness distribution of a combined beam shaper and bowtie filter.

In FIGS. 5 to 7, the thickness is given in units of line integrals, i.e., as filter thickness times attenuation coefficient, For example, if the filter material is Teflon with an attenuation coefficient of 0.021/mm at 80 keV, about 48 mm thickness is equivalent to a line integral of 1.

Figure 8:
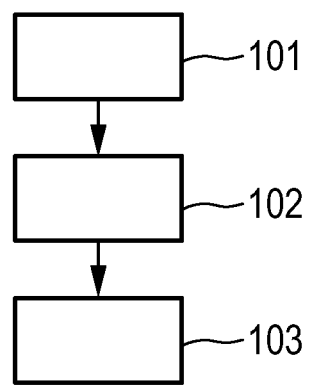
FIG. 8 shows a flowchart exemplarily illustrating a computed tomography method.

In the following a computed tomography method will be described with reference to a flowchart shown in FIG. 8.

In step 101, the radiation source 2 rotates around the rotational axis R and the object or the examination region 5 is moved in the direction of the rotational axis R to rotate the radiation source 2 and the examination region 5 relative to each other along a helical trajectory. The radiation source 2 emits radiation, which is collimated to a conical radiation beam by a collimator, shaped by a beam shaper and traverses the examination region 5 of the computed tomography apparatus. The radiation, which has traversed the object or the examination region 5, is detected by the detector 6 which generates detection values depending on the conical radiation beam. The conical radiation beam, the detector and the helical trajectory are chosen such that redundant detection values are acquired.

In step 102, for combinations of voxels of an image of the examination region and redundant detection values normalized weights for weighting the redundant detection values are provided by the weight providing unit 12. In step 103, the reconstruction unit 13 reconstructs the voxels, wherein for reconstructing a voxel following steps are performed: i) weighting redundant detection values, which correspond to the voxel to be reconstructed, wherein the redundant detection values are multiplied with the weights, in particular, the normalized weights, provided for the combinations of the voxel to be reconstructed and the corresponding redundant detection values, and ii) reconstructing the voxel from the weighted redundant detection values. In step 103, the step of reconstructing the voxel is preferentially performed by using a backprojection algorithm. In an embodiment, firstly the weighting is performed for all redundant detection values, i.e. step i) is performed for all redundant detection values, and then the voxels are reconstructed, i.e. step ii) is performed for all voxels to be reconstructed.

In step 101, the conical radiation beam is shaped such that for at least a part of the detection values the inverse of the variance of a respective detection value is positively correlated with an average of the normalized weights corresponding to the combination of the voxels, which correspond to the respective detection value, and the respective detection value.

In an embodiment, before acquiring the detection values in step 101, a collimation and/or a pitch of a helical trajectory can be chosen, wherein a beam shaper is selected depending on the chosen collimation and/or pitch, respectively, and wherein the selected beam shaper is used while acquiring the detection values.

The bowtie filter is preferentially adapted to shape the conical radiation beam such that more photons are emitted towards the isocenter of the computed tomography apparatus than to the periphery of the examination region. This leads to a better dose utility since typically rays near the isocenter are attenuated much more than peripheral rays. The computed tomography apparatus can comprise several separate bowtie filters, which can be regarded as the second kind of beam shaper, and/or the computed tomography apparatus can comprise several beam shapers, which can be regarded as being of the first kind of beam shapers, wherein these beam shapers also fulfill the function of a bowtie filter, i.e. these beam shapers can be regarded as bowtie filters being modified to shape the conical radiation beam such that for at least a part of the detection values the inverse of the variance of a respective detection value is positively correlated with an average of the normalized weights corresponding to the combination of the voxels, which correspond to the respective detection value, and the respective detection value.

The shape of the beam along the rotational axis is preferentially designed such that a homogenous illumination of detector rows is achieved.

During reconstruction x-rays from different detector rows and columns are preferentially averaged if they contain essentially redundant information. This averaging is preferentially not performed in a way that the signal-to-noise ratio is optimized. This averaging is a weighted averaging, wherein the weighting is preferentially tuned to balance signal-to-noise ratio, motion artifacts, and cone-beam artifacts. This is preferentially achieved by using by a so-called aperture weighted wedge reconstruction, where detection values with a larger aperture are weighted less than detection values with a smaller aperture.

FIG. 4 shows schematically and exemplarily averaged normalized weights for a helical scan with a pitch of one. If these averaged normalized weights are considered as desired from the perspective of suppressing motion and cone-beam artifacts, from these averaged normalized weights a desired signal-to-noise ratio distribution on the detector surface can be derived. If data $\alpha_1, \ldots, \alpha_n$ with uncertainties $\sigma_1, \ldots, \sigma_n$ are given, an average of these data $\alpha_1, \ldots, \alpha_n$ is preferentially calculated with relative weights $1/\sigma_1^2, \ldots, 1/\sigma_n^2$ in order to achieve the best possible signal-to-noise ratio of the average. Therefore, the dose utility of the computed tomography apparatus can be improved, if the conical radiation beam is shaped such that the expected inverse variances of the data, i.e. of the detection values, match these relative weights.

Although an analytical reconstruction, in particular, an aperture weighted wedge reconstruction, is mentioned above, the computed tomography apparatus can also be adapted to perform another reconstruction, for example, to perform an iterative reconstruction. If an iterative reconstruction is performed, preferentially an aperture weighting is used in order to suppress motion artifacts and to achieve a good convergence behavior. The optimal shape of the beam may differ if a different reconstruction algorithm is used. In an embodiment, the computed tomography apparatus can be adapted to choose a reconstruction algorithm, automatically or by a user, wherein the computed tomography apparatus is preferentially adapted to choose a beam shaper which corresponds to the chosen reconstruction algorithm, wherein the chosen beam shaper is used while acquiring the detection values.

As already mentioned above, the beam shaper preferentially depends on the collimation and/or the pitch of a helical trajectory. If the computed tomography apparatus only comprises a single beam shaper with a separate or integrated bowtie filter, the use of this beam shaper may be directly linked to specific low-dose protocols.

The material of the beam shaper is preferentially a "soft" material in order to avoid beam hardening. The beam shaper is preferentially made of Teflon. Also the bowtie filter is preferentially made of Teflon. A "soft" material is preferentially a material having a spectral dependence of the attenuation coefficient, which is similar to the spectral dependence of the main constituent of the object to be reconstructed, for example, to the spectral dependence of the main constituent of a human body, namely water.

The beam shaper has preferentially a maximum thickness equal to or smaller than 10 cm and further preferred equal to or smaller than 5 cm. In a preferred embodiment the beam shaper has a maximum thickness of 4 cm.

Figure 9:
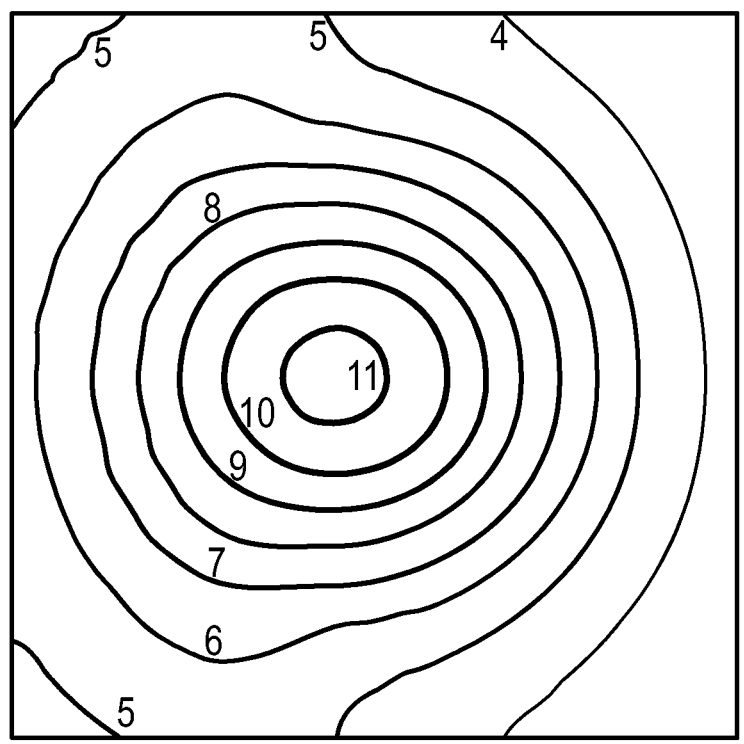
FIG. 9 shows exemplarily a contour line plot of a noise level within an image which has been reconstructed based on detection values which have been acquired without using a beam shaper in accordance with the invention.
Figure 10:
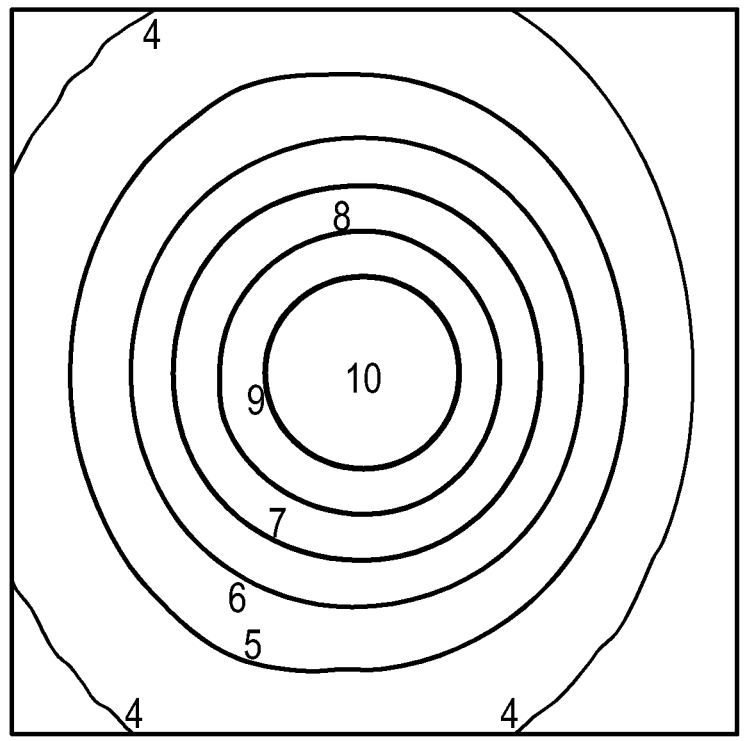
FIG. 10 shows exemplarily a contour line plot of a noise level within an image which has been reconstructed based on detection values which have been acquired with using an optimal beam shaper in accordance with the invention.
Figure 11:
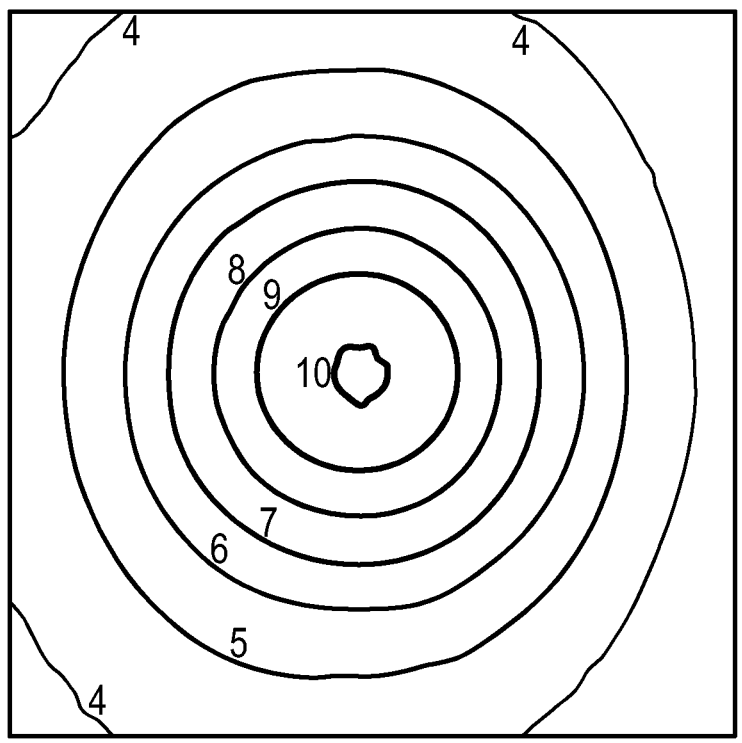
FIG. 11 shows exemplarily a contour line plot of a noise level within an image which has been reconstructed based on detection values which have been acquired with using a non-optimal beam shaper in accordance with the invention.

FIG. 9 shows schematically and exemplarily a contour line plot of the noise value in Hounsfield units of an image of a spherical object which has been reconstructed based on detection values, which have been acquired without using a beam shaper in accordance with the invention. In FIG. 9, the numbers indicate noise levels of the respective line connecting voxels with the same noise level. FIG. 10 shows a corresponding noise level distribution in Hounsfield units, which relates to a reconstruction of the same spherical element from detection values which have been acquired while an optimal beam shaper in accordance with the invention has been used. An optimal beam shaper in accordance with the invention is a beam shaper being adapted to shape the conical radiation beam such that for all detection values the inverse of the variance of a respective detection value is positively correlated with an average of the normalized weights corresponding to the combination of the voxels, which correspond to the respective detection value, and the respective detection value. FIG. 11 shows a noise level distribution in Hounsfield units, which relates to a reconstruction of an image of the spherical object from detection values which have been acquired while a non-optimal beam shaper in accordance with the invention has been used. A non-optimal beam shaper in accordance with the invention is adapted to shape the conical radiation beam such that for a part, i.e. not all, of the detection values the inverse of the variance of a respective detection value is positively correlated with an average of the normalized weights corresponding to the combination of the voxels, which correspond to the respective detection value, and the respective detection value. The non-optimal beam shaper, which has been used for acquiring the detection values which led to FIG. 11, has a maximum thickness of 4 cm.

The noise level distribution shown in FIG. 9 is more asymmetric than the noise level distributions shown in FIGS. 10 and 11. It should be noted that FIGS. 9 to 11 show a slice of a three-dimensional noise level distribution, wherein the slice is located perpendicular to the rotational axis R. If a user reviews a corresponding three-dimensional image slice by slice, the noise level distribution shown in FIG. 9 rotates around the center of the noise level distribution. This reduces the quality of the three-dimensional image. Since the noise level distributions illustrated in FIGS. 10 and 11 show a larger degree of rotational symmetry, the influence of the rotating noise level distribution, while reviewing different slices, on the image quality is reduced. Thus, the use of a beam filter in accordance with the invention improves the image quality.

Figure 12:
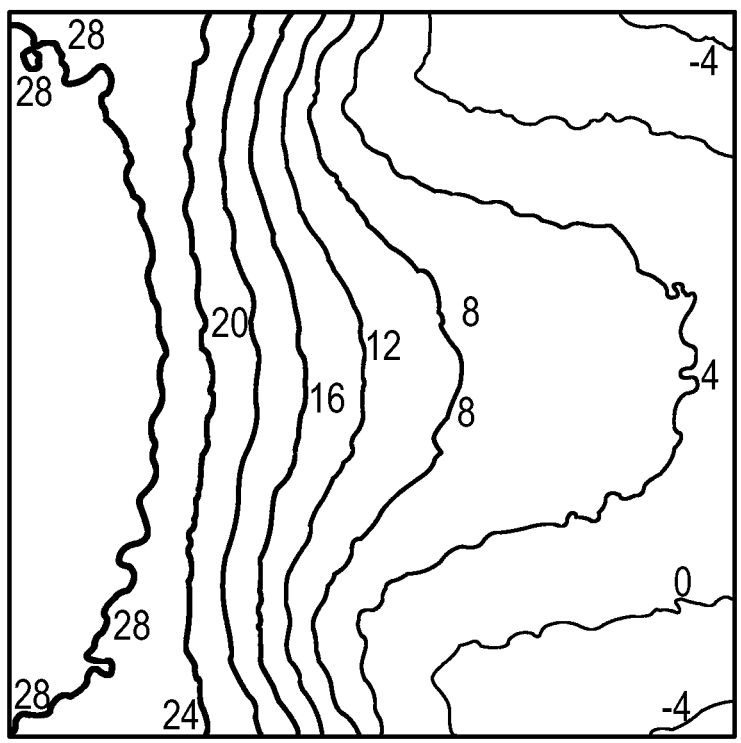
FIG. 12 shows exemplarily a contour line plot of signal-to-noise ratio improvements in an image which has been reconstructed based on detection values which have been acquired while the optimal beam shaper is used.
Figure 13:
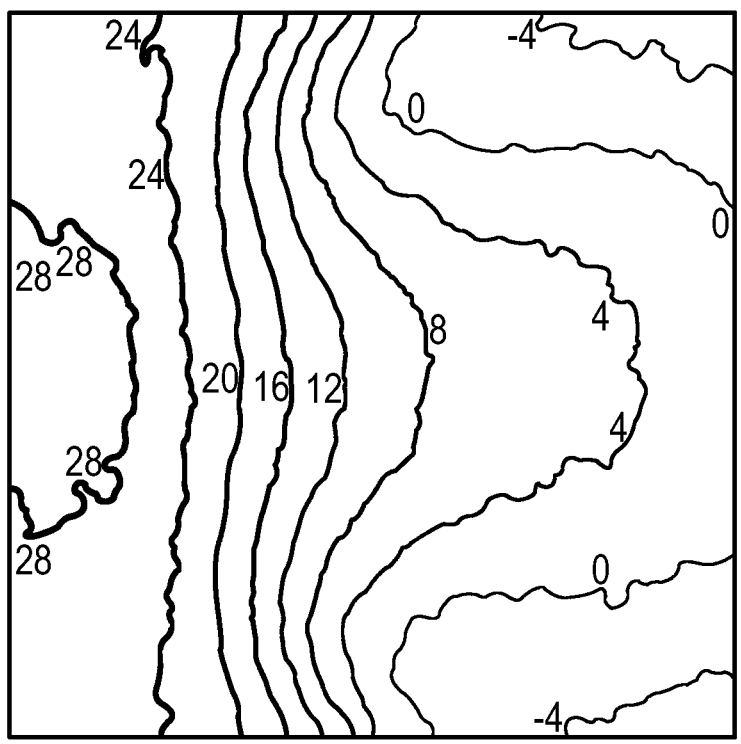
FIG. 13 shows exemplarily a contour line plot of signal-to-noise ratio improvements in an image which has been reconstructed based on detection values which have been acquired while the non-optimal beam shaper is used.

FIG. 12 shows schematically and exemplarily the improvement of the signal-to-noise ratio in percent, if the optimal beam shaper is used, in comparison to a signal-to-noise ratio obtained if a beam shaper in accordance with the invention is not used. FIG. 12 is a contour line plot, wherein values on the image having the same signal-to-noise ratio improvement are connected by the same contour line. FIG. 13 shows a corresponding contour line plot for the non-optimal beam shaper. In this embodiment, as it can be seen in FIGS. 12 and 13, by using the beam shaper a signal-to-noise ratio improvement being larger than 28 percent is obtained.

Figure 14:
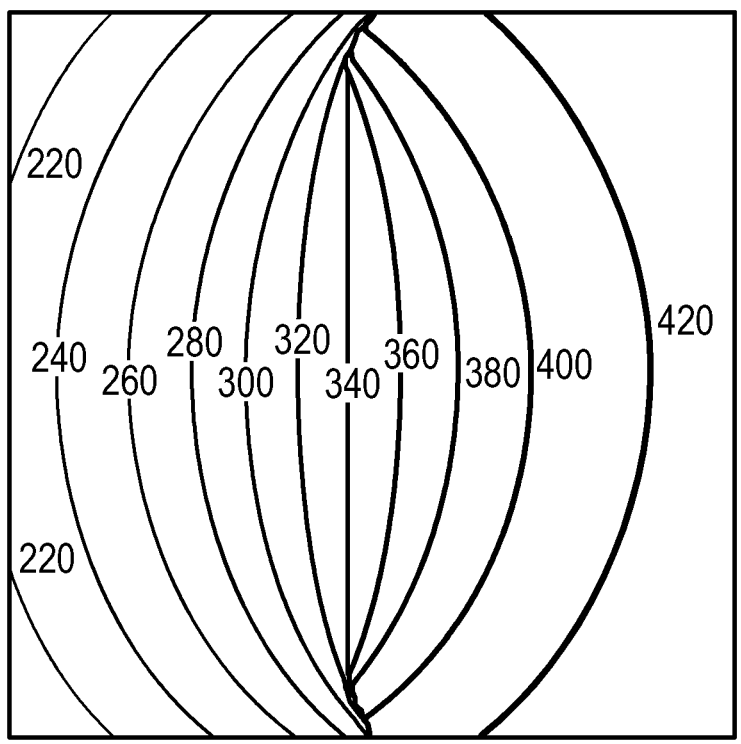
FIG. 14 shows exemplarily a contour line plot of an illumination window width for different locations within an image of an examination region.

FIG. 14 shows schematically and exemplarily a contour line plot which shows for different voxels in a slice of a three-dimensional image of the examination region the angular illumination window width. The illumination window width is defined as the angular range over which a voxel stays within the cone. For FIG. 14, a pitch of one was assumed.

Since in FIG. 14 from the left side to the right side the illumination window width substantially increases, from the left side to the right side in FIG. 14 the signal-to-noise ratio also increases. As it can be seen in FIGS. 12 and 13 the signal-to-noise ratio improvement is larger on the left side than on the right side, if the beam shaper in accordance with the invention is used. Thus, the use of the beam shaper results in larger signal-to-noise ratio improvements, in regions of the image in which the signal-to-noise ratio is smaller, and in smaller signal-to-noise ratio improvements, in regions of the image, in which the signal-to-noise ratio is larger. This leads to a more homogeneous signal-to-noise ratio distribution across the image and improves therefore further the quality of the reconstructed image.

Although in the above described embodiments a collimation and shaping unit is provided comprising a collimator, a beam shaper with an integrated bowtie filter or a beam shaper with a separate bowtie filter, these beam shapers and filters and the collimator can also be elements which are not combined into a collimation and shaping unit. Moreover, the beam shaper exchange unit can be located outside a collimation and shaping unit, and can also be provided, if the beam shaper is not part of a collimation and shaping unit.

Although in the above described embodiments, the collimator and the beam shaper and/or the bowtie filer are arranged such that the radiation beam is collimated by the collimator before being incident on the beam shaper and/or bowtie filer, in other embodiments the collimator and the beam shaper and/or the bowtie filter can be arranged such that the radiation beam is incident on the beam shaper and/or bowtie filter before being collimated by the collimator.

Although in the above described embodiments the weights for weighting the detection values are normalized weights, in other embodiments also weights can be used, which are not normalized. Moreover, although in the above described embodiments redundant detection values have been weighted, is it also possible that detection values are weighted, which are not redundant.

If redundant detection values and non-redundant detection values have been acquired, the reconstruction unit is preferentially adapted to reconstruct an image of the examination region from the redundant detection values, which are weighted, and from the non-redundant detection values, which may also be weighted. In particular, before reconstruction, i.e., for example, before backprojecting, the redundant detection values can be weighted by the above described weights, preferentially by the above mentioned normalized weights wherein the sum of the weights of the detection values which correspond to the same voxel is one, and the non-redundant detection values are preferentially weighted with one or not weighted Although an aperture weighted wedge reconstruction method has been mentioned above, an image of the examination region can be reconstructed also by using another reconstruction method. For example, a maximum likelihood iterative reconstruction method as, for instance, disclosed in the article "Correction of Iterative Reconstruction Artifacts in Helical Cone-Beam CT", Zeng, K. et al., 10$^{th}$ International Meeting on Fully Three-Dimensional Image Reconstruction in Radiology and Nuclear Medicine, pages 242-245 can be used. Also the aperture weighted wedge reconstruction method disclosed in "Weighted FBP—a simple approximate 3D FBP algorithm for multislice spiral CT with good dose usage for arbitrary pitch", Stierstorfer K. et al., Phys. Med. Biol, volume 49, pages 2209-2218, 2004 can be used. Furthermore an angular weighted parallel beam backprojection as disclosed in, for example, "Extended parallel backprojection for standard three-dimensional and phase-correlated four-dimensional axial and spiral cone-beam CT with arbitrary pitch, arbitrary cone-angle, and 100% dose usage", Kachelriess, M. et al., Med. Phys., volume 31, pages 1623-1641, 2004, a weighted cone-beam computed tomography reconstruction method as disclosed in "A new weighting scheme for cone-beam helical CT to reduce the image noise", Taguchi, K. et al., Phys. Med. Biol., volume 49, pages 2351-2364, 2004 or reconstruction methods based on two-dimensional approximations like the ASSR method, which is, for example, disclosed in "Advanced single-slice rebinning in cone-beam spiral CT", Kachelriess, M. et al., Med. Phys., volume 27, pages 754-772, 2000 can be used for reconstructing an image of the examination region.

If in the above described embodiments it is mentioned that the beam shaper is adapted to shape the conical radiation beam such that for at least a part of the detection values the inverse of the variance of a respective detection value is positively correlated with an average of the weights corresponding to the combinations of the voxels, which correspond to the respective detection value, and the respective detection value, preferentially the beam shaper is adapted to shape the conical radiation beam such that for at least a part of the detection values the inverse of the variance of a respective detection value is similar to an average of the weights corresponding to the combinations of the voxels, which correspond to the respective detection value, and the respective detection value.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

The provision of the weights performed by the weight providing unit and the reconstruction of the voxels of an image of the examination region performed by the reconstruction unit can be performed by any other number of units or devices. For example, the provision of the weights and the reconstruction can be performed by a single unit or by any other number of different units. The provision of the weights and the reconstruction and/or the control of the computed tomography apparatus in accordance with the computed tomography method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a computed tomography apparatus comprising a radiation source and a detector for generating detection values depending on a conical radiation beam. A weight providing unit provides, for combinations of voxels of an image and detection values, weights for weighting the detection values, and a beam shaper shapes the conical radiation beam such that for at least a part of the detection values the inverse of the variance of a respective detection value is positively correlated with an average of the weights corresponding to the combinations of the voxels, which correspond to the respective detection value, and the respective detection value. This shaping of the conical radiation beam improves the signal-to-noise ratio of the weighted detection values.

The invention claimed is:

1. A computed tomography apparatus, the computed tomography apparatus comprising:
   a radiation source for emitting a conical radiation beam for traversing an examination region of the computed tomography apparatus,
   a beam shaper for shaping the conical radiation beam,
   a detector for generating detection values depending on the conical radiation beam after having traversed the examination region,
   a weight providing unit for providing, for combinations of voxels of an image of the examination region and detection values, wherein each combination comprise a voxel and a detection value which corresponds to the voxel, weights for weighting the detection values, a reconstruction unit for reconstructing the voxels, wherein for reconstructing a voxel the reconstruction unit is adapted to weight the detection values, which correspond to the voxel to be reconstructed, with the weights provided for the combinations of the voxel to be reconstructed and the respective corresponding detection value, and to reconstruct the voxel from the weighted detection values, wherein the beam shaper is adapted to shape the conical radiation beam such that for at least a part of the detection values an average of the weights corresponding to the combinations of the voxels, which correspond to the respective detection value, and the respective detection value is positively correlated with the intensity of the respective part of the conical radiation beam, on which the respective detection value depends, before traversing the examination region.

2. The computed tomography apparatus as defined in claim 1, wherein the radiation source and the detector are adapted to detect redundant detection values, the weight providing unit is adapted to provide, for combinations of voxels of an image of the examination region and redundant detection values, normalized weights for weighting the redundant detection values, for reconstructing a voxel the reconstruction unit is adapted to weight the redundant detection values, which correspond to the voxel to be reconstructed, with the normalized weights provided for the combinations of the voxel to be reconstructed and the respective corresponding redundant detection value, and to reconstruct the voxel from the weighted redundant detection values, the beam shaper is adapted to shape the conical radiation beam such that for at least a part of the redundant detection values an average of the weights corresponding to the combination of the voxels, which correspond to the respective redundant detection value, and the respective redundant detection value is positively correlated with the intensity of the respective part of the conical radiation beam, on which the respective detection value depends, before traversing the examination region.

3. The computed tomography apparatus as defined in claim 1, wherein the weight providing unit is adapted to provide the weights such that cone-beam artifacts are reduced.

4. The computed tomography apparatus as defined in claim 1, wherein the weight providing unit is adapted to provide the weights such that motion artifacts are reduced.

5. The computed tomography apparatus as defined in claim 1, wherein the weight providing unit is adapted to provide a weight for a combination of a voxel and a detection value depending on an aperture of the part of the conical radiation beam, which has traversed the voxel and on which the depending detection value has been generated.

6. The computed tomography apparatus as defined in claim 5, wherein the weight providing unit is adapted to provide a larger weight, if the aperture is smaller, and a smaller weight, if the aperture is larger.

7. The computed tomography apparatus as defined in claim 6, wherein the weight providing unit is adapted to provide the weights such that the weights of the detection values continuously and monotonically approach zero with increasing aperture.

8. The computed tomography apparatus as defined in claim 1, wherein the computed tomography apparatus comprises a moving unit for moving the radiation source and the examination region relative to each other along a helical trajectory, wherein the weight providing unit is adapted to provide the weights depending on a pitch of the helical trajectory, wherein the computed tomography apparatus comprises several beam shapers for different pitches and is adapted to choose a beam shaper from the several beam shapers depending on the pitch of the helical trajectory and to use the chosen beam shaper while generating the detection values.

9. The computed tomography apparatus as defined in claim 1, wherein the computed tomography apparatus comprises a collimator for collimating the conical radiation beam, wherein the weight providing unit is adapted to provide the weights depending on a collimation of the conical radiation beam, wherein the computed tomography apparatus comprises several beam shapers for different collimations and is adapted to choose a beam shaper from the several beam shapers depending on the collimation of the conical radiation beam and to use the chosen beam shaper while generating the detection values.

10. The computed tomography apparatus as defined in claim 1, wherein the beam shaper is a bowtie filter.

11. The computed tomography apparatus as defined in claim 1, wherein the computed tomography apparatus further comprises a second kind of beam shaper being a bowtie filter.

12. A beam shaper for being used with a computed tomography apparatus as defined in claim 1, wherein the beam shaper is adapted to shape the conical radiation beam such that for at least a part of the detection values an average of the weights corresponding to the combination of the voxels, which correspond to the respective detection value, and the respective detection value is positively correlated with the intensity of the respective part of the conical radiation beam, on which the respective detection value depends, before traversing the examination region.

13. A computed tomography method, the computed tomography method comprising the following steps:

emitting a conical radiation beam for traversing an examination region (5) of a computed tomography apparatus by a radiation source, shaping the conical radiation beam by a beam shaper, generating detection values depending on the conical radiation beam after having traversed the examination region by a detector, providing, for combinations of voxels of an image of the examination region and detection values, wherein each combination comprises a voxel and a detection value which corresponds to the voxel, weights for weighting the detection values by a weight providing unit, reconstructing the voxels by a reconstruction unit, wherein for reconstructing a voxel the detection values, which correspond to the voxel to be reconstructed, are weighted with the weights provided for the combinations of the voxel to be reconstructed and a respective corresponding redundant detection value, and the voxel is reconstructed from the weighted detection values, wherein the conical radiation beam is shaped such that for at least a part of the detection values an average of the weights corresponding to the combinations of the voxels, which correspond to the respective detection value, and the respective detection value is positively correlated with the intensity of the respective part of the conical radiation beam, on which the respective detection value depends, before traversing the examination region.

14. A computed tomography computer program stored on a non-transitory computer readable medium, the computed tomography computer program comprising program code means for causing a computed tomography apparatus to carry out the steps of the computed tomography method as defined in claim 13, when the computed tomography computer program is run on a computer controlling the computed tomography apparatus.

* * * * *